(12) United States Patent
Chen

(10) Patent No.: US 10,663,423 B2
(45) Date of Patent: *May 26, 2020

(54) SYSTEM FOR DETECTING ELECTRICAL PROPERTIES OF A MOLECULAR COMPLEX

(71) Applicant: Roche Sequencing Solutions, Inc., Pleasanton, CA (US)

(72) Inventor: Roger J. A. Chen, Saratoga, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/183,618

(22) Filed: Nov. 7, 2018

(65) Prior Publication Data

US 2019/0154623 A1 May 23, 2019

Related U.S. Application Data

(63) Continuation of application No. 15/819,994, filed on Nov. 21, 2017, now Pat. No. 10,156,541, which is a (Continued)

(51) Int. Cl.
*G01N 27/30* (2006.01)
*G01N 27/327* (2006.01)
(Continued)

(52) U.S. Cl.
CPC ....... *G01N 27/3278* (2013.01); *C12Q 1/6874* (2013.01); *G01N 27/44791* (2013.01); *G01N 33/48721* (2013.01)

(58) Field of Classification Search
None
See application file for complete search history.

(56) References Cited

U.S. PATENT DOCUMENTS 8,962,242 B2 * 2/2015 Chen ............... G01N 33/48721
435/6.1
9,581,563 B2 2/2017 Chen
(Continued)

FOREIGN PATENT DOCUMENTS

GB 1120706 A 7/1968
WO WO 2008/124706 A2 * 4/2008 ............. C12M 3/00

OTHER PUBLICATIONS

Mollazadeh et al, IEEE Tran Biomed Circuits Syst., pp. 1-13 (2009).*

*Primary Examiner* — Robert T. Crow
(74) *Attorney, Agent, or Firm* — Roche Sequencing Solutions, Inc.

(57) ABSTRACT

A system for detecting electrical properties of a molecular complex is disclosed. The system includes an electrode electrically coupled to a molecular complex that outputs an electrical signal affected by an electrical property of the molecular complex, wherein the effect of the electrical property of the molecular complex on the electrical signal is characterized by an expected bandwidth. The system further includes an integrating amplifier circuit configured to receive the electrical signal from the electrode. The integrating amplifier circuit is further configured to selectively amplify and integrate a portion of the electrical signal over time within a predetermined bandwidth, wherein the predetermined bandwidth is selected at least in part based on the expected bandwidth.

11 Claims, 6 Drawing Sheets

Related U.S. Application Data continuation of application No. 14/558,268, filed on Dec. 2, 2014, now Pat. No. 9,869,655, which is a continuation of application No. 13/272,128, filed on Oct. 12, 2011, now Pat. No. 8,962,242.

(60) Provisional application No. 61/435,700, filed on Jan. 24, 2011.

(51) Int. Cl.
*G01N 33/487* (2006.01)
*C12Q 1/6874* (2018.01)
*G01N 27/447* (2006.01)

(56) References Cited

U.S. PATENT DOCUMENTS

| | | | |
|---|---|---|---|
| 9,869,655 B2 * | 1/2018 | Chen | G01N 33/48721 |
| 10,156,541 B2 * | 12/2018 | Chen | G01N 33/48721 |
| 10,330,633 B2 * | 6/2019 | Chen | G01N 33/48721 |
| 2006/0063202 A1 | 3/2006 | Pieribone | |
| 2007/0202495 A1 * | 8/2007 | Mayer | G01N 33/48721 |
| | | | 435/5 |
| 2008/0171316 A1 * | 7/2008 | Golovchenko | C12Q 1/6869 |
| | | | 435/6.11 |
| 2010/0084276 A1 * | 4/2010 | Lindsay | C12Q 1/6869 |
| | | | 205/93 |

* cited by examiner

SYSTEM FOR DETECTING ELECTRICAL PROPERTIES OF A MOLECULAR COMPLEX

CROSS REFERENCE TO OTHER APPLICATIONS

This application is a continuation of co-pending U.S. patent application Ser. No. 15/819,994, entitled SYSTEM FOR DETECTING ELECTRICAL PROPERTIES OF A MOLECULAR COMPLEX, filed Nov. 21, 2017, which is a continuation of U.S. patent application Ser. No. 14/558,268, now U.S. Pat. No. 9,869,655, entitled SYSTEM FOR DETECTING ELECTRICAL PROPERTIES OF A MOLECULAR COMPLEX, filed Dec. 2, 2014, which is a continuation of U.S. patent application Ser. No. 13/272,128, now U.S. Pat. No. 8,962,242, entitled SYSTEM FOR DETECTING ELECTRICAL PROPERTIES OF A MOLECULAR COMPLEX, filed Oct. 12, 2011, which claims priority to U.S. Provisional Patent Application No. 61/435,700, entitled SYSTEM FOR COMMUNICATING INFORMATION FROM AN ARRAY OF SENSORS, filed Jan. 24, 2011, all of which are incorporated herein by reference for all purposes.

BACKGROUND OF THE INVENTION

Advances in micro-miniaturization within the semiconductor industry in recent years have enabled biotechnologists to begin packing their traditionally bulky sensing tools into smaller and smaller form factors, onto so-called biochips. It would be desirable to develop techniques for biochips.

BRIEF DESCRIPTION OF THE DRAWINGS

Various embodiments of the invention are disclosed in the following detailed description and the accompanying drawings.

DETAILED DESCRIPTION

Figure 1:
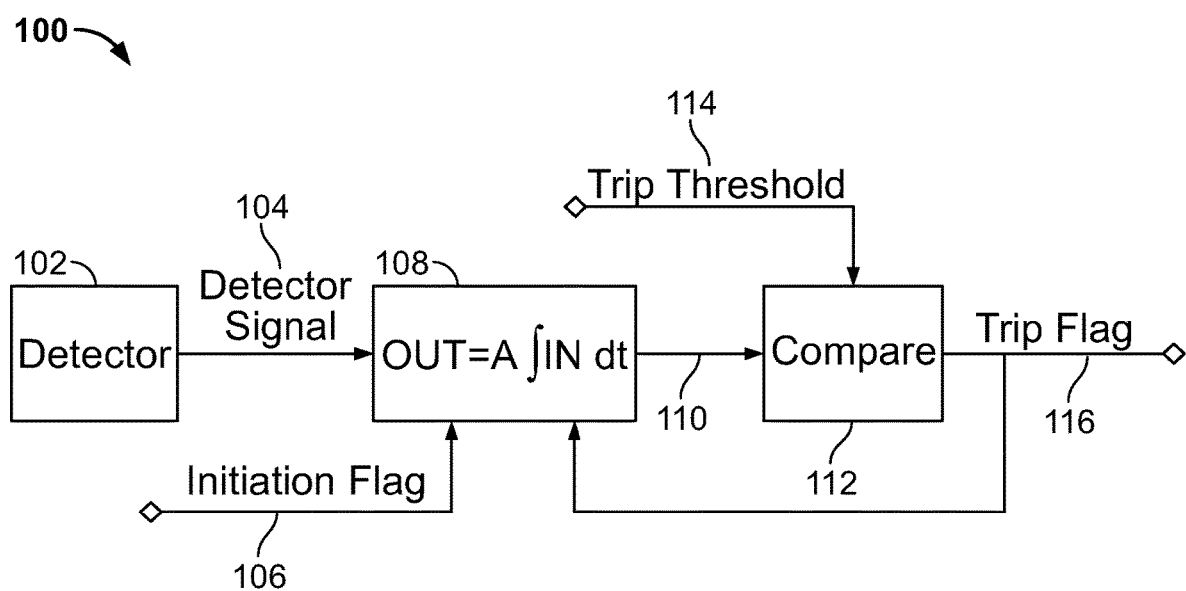
FIG. 1 is a block diagram illustrating an embodiment of a sensor circuit 100 for measuring a physical property within a single cell in a biochip.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

In various embodiments, the techniques described herein are implemented in a variety of systems or forms. In some embodiments, the techniques are implemented in hardware as an application-specific integrated circuit (ASIC) or a field-programmable gate array (FPGA). In some embodiments, a processor (e.g., an embedded one such as an ARM core) is used where the processor is provided or loaded with instructions to perform the techniques described herein. In some embodiments, the technique is implemented as a computer program product which is embodied in a computer readable storage medium and comprises computer instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Advances in micro-miniaturization within the semiconductor industry in recent years have enabled biotechnologists to begin packing their traditionally bulky sensing tools into smaller and smaller form factors, onto so-called biochips. These chips are essentially miniaturized laboratories that can perform hundreds or thousands of simultaneous biochemical reactions. Biochips enable researchers to quickly screen large numbers of biological analytes for a variety of purposes, from disease diagnosis to detection of bioterrorism agents.

Typically, a biochip includes a large array of cells. For example, a biochip for nucleotide sequencing may contain thousands or millions of single cells in an array. Each cell includes a molecular complex composed of monomers that make up an oligomeric nanopore and a single strand of DNA, and anything bound to that single strand of DNA. The nanopore is a small hole in an electrically insulating membrane that can be used as a single-molecule detector. A nanopore may be formed using a biological material, such as α-hemolysin or MspA. A nanopore may be formed using a solid-state material, such as a semiconductor material. When a small voltage is applied across a molecular complex containing a nanopore, an ionic current through the molecular complex can be measured to provide information about the structure of a molecule transiting the molecular complex. In a single cell of the array, an electrical circuit may be used for controlling the electrical stimulus applied across a lipid bilayer which contains a nanopore, and for detecting the electrical patterns, or signatures, of a molecule passing through the nanopore. These patterns or signatures identify events of interest such as additions or subtractions to the molecular complex, or conformational changes to the molecular complex. In order to reduce the cost of the array, physically small single cells with highly sensitive sensors therein are desirable.

FIG. 1 is a block diagram illustrating an embodiment of a sensor circuit 100 for measuring a physical property within a single cell in a biochip. As shown in FIG. 1, a physical property, e.g., a current, voltage, or charge, is detected by detector 102 as detected signal 104. Sensor circuit 100 may be used to measure the mean value of detected signal 104 without sampling as described further below.

In some embodiments, an initiation flag 106 resets an integrating amplifier 108 and starts a continuous integration of detected signal 104 over time. Integrated output 110 is compared with a trip threshold 114 using a comparator 112. When integrated output 110 reaches trip threshold 114, a trip flag 116 may be used as a feedback signal to integrating amplifier 108 for terminating the integration of detected signal 104. For example, when trip flag 116 is "on" or asserted, the integration is terminated. The duration of time between the assertion of initiation flag 106 and the assertion of trip flag 116 is proportional to the mean value of detected signal 104, e.g., the mean value of a current. Accordingly, the "on" and "off" of trip flag 116 (only 1 bit of information) may be sent from the cell to an external processor for calculating the mean value of detected signal 104. Alternatively, the "on/off" information may be sent from the cell to an external storage for delayed processing. For example, the clock cycles at which initiation flag 106 and trip flag 116 are respectively asserted may be recorded in an external storage. The number of clock cycles between the two asserted flags may then be used to determine the mean value of detected signal 104 at a later time.

In some embodiments, more accurate results may be obtained by integrating detected signal 104 over multiple integrating cycles. For example, the determined mean value of detected signal 104 may be further averaged over multiple integrating cycles. In some embodiments, initiation flag 106 is based at least in part on trip flag 116. For example, initiation flag 106 may be re-asserted in response to trip flag 116 being asserted. In this example, trip flag 116 is used as a feedback signal for reinitializing integrating amplifier 108, such that another cycle of integration of detected signal 104 may begin as soon as the previous cycle of integration is terminated. Re-asserting initiation flag 106 immediately after trip flag 116 is asserted reduces the portion of time when detector 102 generates a signal that is not integrated and thus not measured. The integration occurs over approximately the entire time that the signal is available. As a result, most of the information of the signal is captured, thereby minimizing the time to obtain an average value for the measured signal.

Shot noise may corrupt trip flag 116 during certain integrating cycles. Accordingly, some embodiments may include logic to determine whether trip flag 116 has been corrupted by shot noise in a particular integrating cycle before trip flag 116 is saved or used for any calculation.

Figure 2:
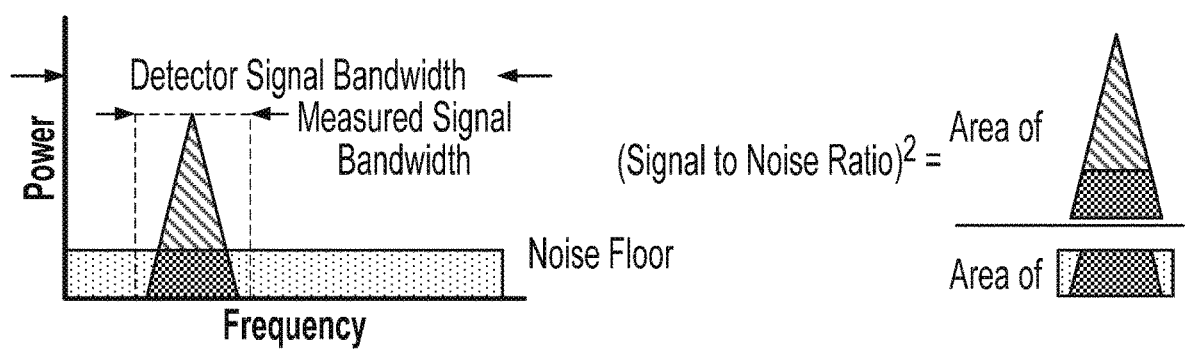
FIG. 2 illustrates that with a constant noise floor, as the measured signal bandwidth decreases, the signal to noise ratio increases, thereby improving the sensitivity of sensor circuit 100 of FIG. 1.

The sensitivity of sensor circuit 100 is maximized by continuously integrating detected signal 102 without sampling. This serves to limit the bandwidth of the measured signal. With continuous reference to FIG. 1, trip threshold 114 and an integration coefficient A set the bandwidth of the measured signal. As integration coefficient A decreases or as trip threshold 114 increases, the measured signal bandwidth decreases. FIG. 2 illustrates that with a constant noise floor, as the measured signal bandwidth decreases, the signal to noise ratio increases, improving the sensitivity of sensor circuit 100. In some embodiments, the measured signal bandwidth can be dynamically adjusted by varying the trip threshold 114.

Figure 3:
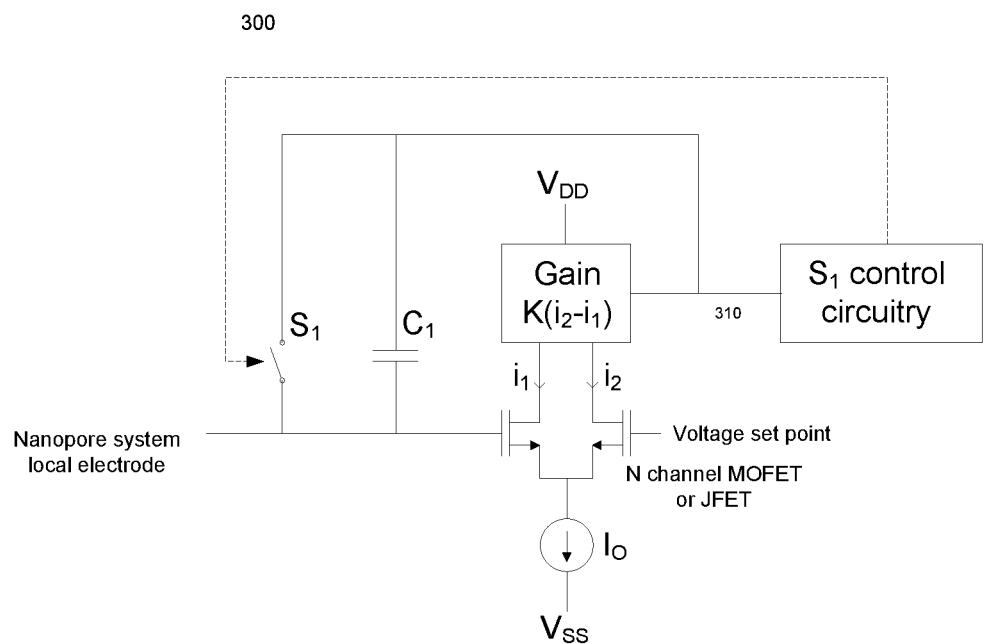
FIG. 3 is a circuit diagram illustrating an embodiment of a sensor circuit 300 for measuring a physical property, e.g., a current, within a single cell in a nanopore array.
Figure 4:
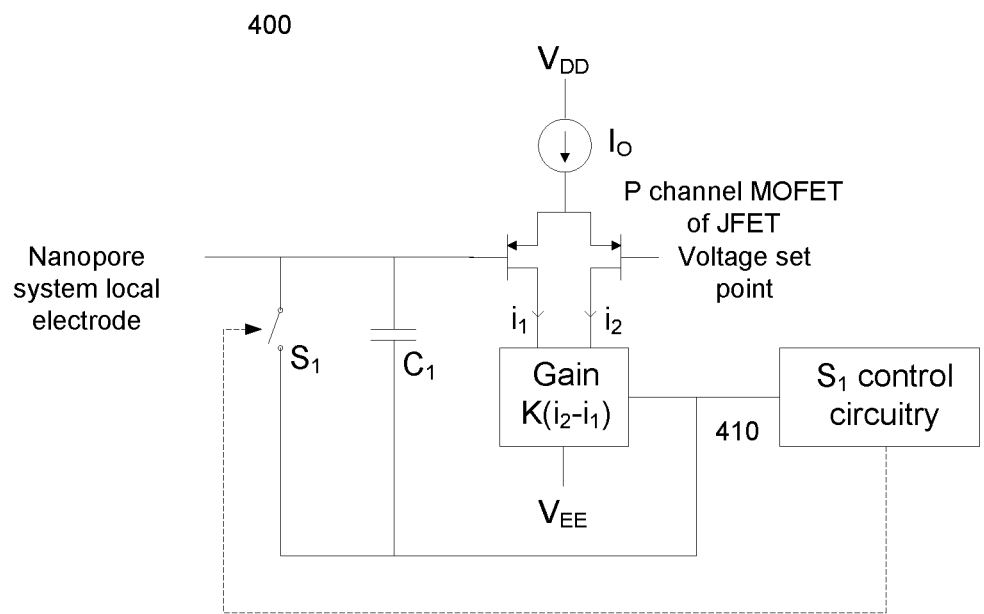
FIG. 4 is a circuit diagram illustrating a second embodiment of a sensor circuit 400 for measuring a physical property within a single cell in a nanopore array.

FIG. 3 is a circuit diagram illustrating an embodiment of a sensor circuit 300 for measuring a physical property, e.g., a voltage, within a single cell in a nanopore array. FIG. 4 is a circuit diagram illustrating a second embodiment of a sensor circuit 400 for measuring a physical property within a single cell in a nanopore array.

With reference to FIGS. 3 and 4, the S1 control circuitry includes a comparator and other logic, e.g., logic for switching. The other components of circuit 300 (or circuit 400), including the differential pair, implement an integrating amplifier similar to that in FIG. 1. The input of circuit 300 (or circuit 400) is connected to a nanopore system local electrode.

Figure 5:
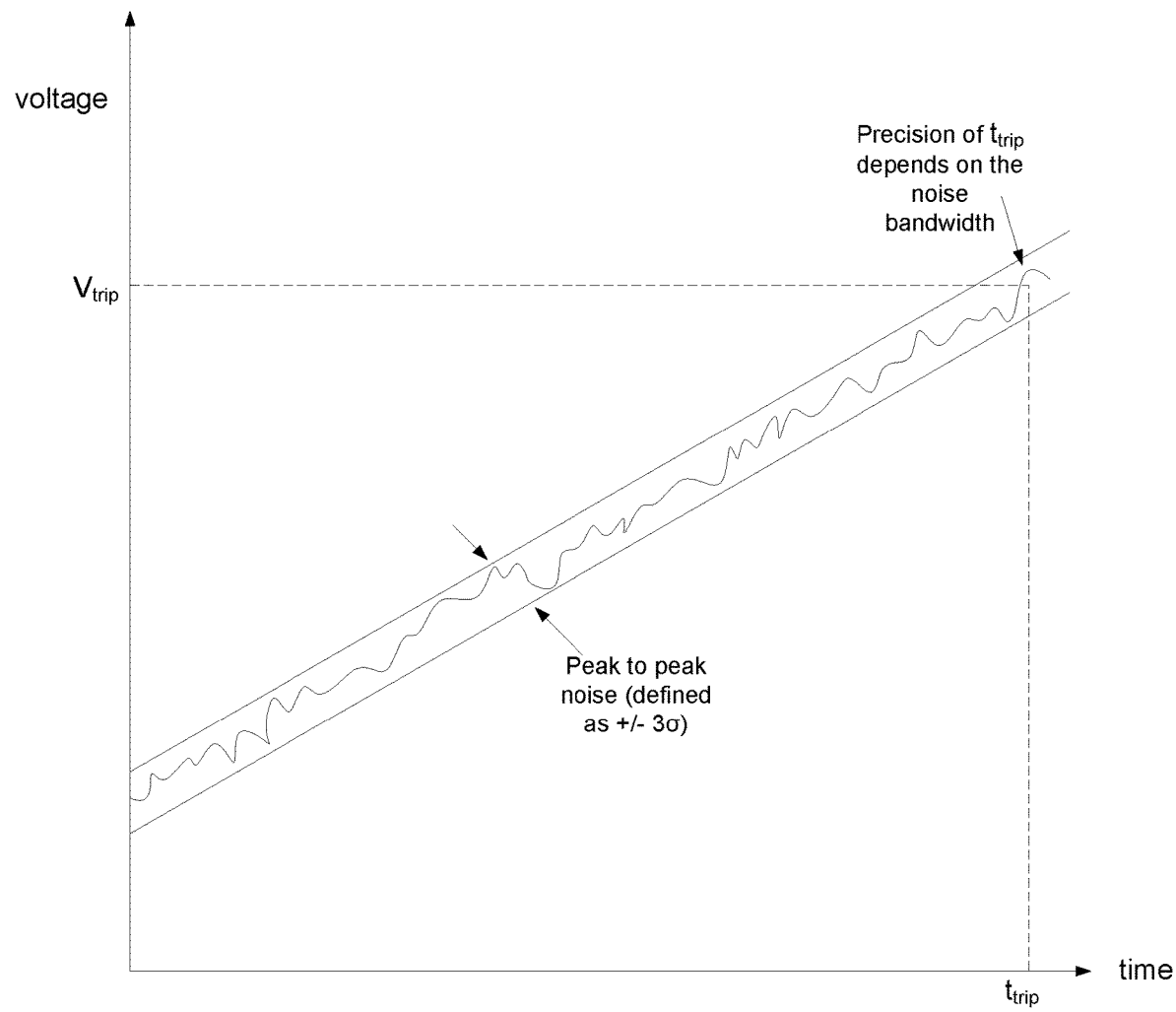
FIG. 5 is a diagram illustrating a plot of the voltage at the output of the integrating amplifier in circuit 300 or circuit 400 versus time.

FIG. 5 is a diagram illustrating a plot of the voltage at 310 (or 410) in circuit 300 (or circuit 400) versus time. In FIG. 5, $t_{trip}$ indicates the mean current flowing through a nanopore. Reducing the noise bandwidth reduces the noise associated with $t_{trip}$. Accordingly, the mean current measurement will have a higher signal to noise ratio (SNR) and be more precise.

The integrating amplifier generates signals within an expected bandwidth containing events of interest of the molecular complex. The integrating amplifier is configured to amplify only signals in the bandwidth of interest, and reject signals outside this bandwidth. Amplifying all signals amplifies mostly noise since the useful signal's bandwidth is much smaller than the detected signal, resulting in poor SNR. The bandwidth of interest may be limited by selecting appropriate values for $C_1$ and $I_O$ in circuits 300 and 400. In some embodiments, $C_1$ and $I_O$ are selected to limit the bandwidth of interest between 0.3 Hz and 300 Hz. In some embodiments, the bandwidth of interest can be dynamically adjusted by varying the values of $C_1$.

In some embodiments, trip flag 116 for each of the cells are further synchronized with a global clock shared by all the cells within the biochip. For example, trip flag 116 that is synchronized with a global clock may be generated by a pulse generation circuit. After synchronization, trip flag 116 is a single pulse that is in phase with the global clock.

Figure 6:
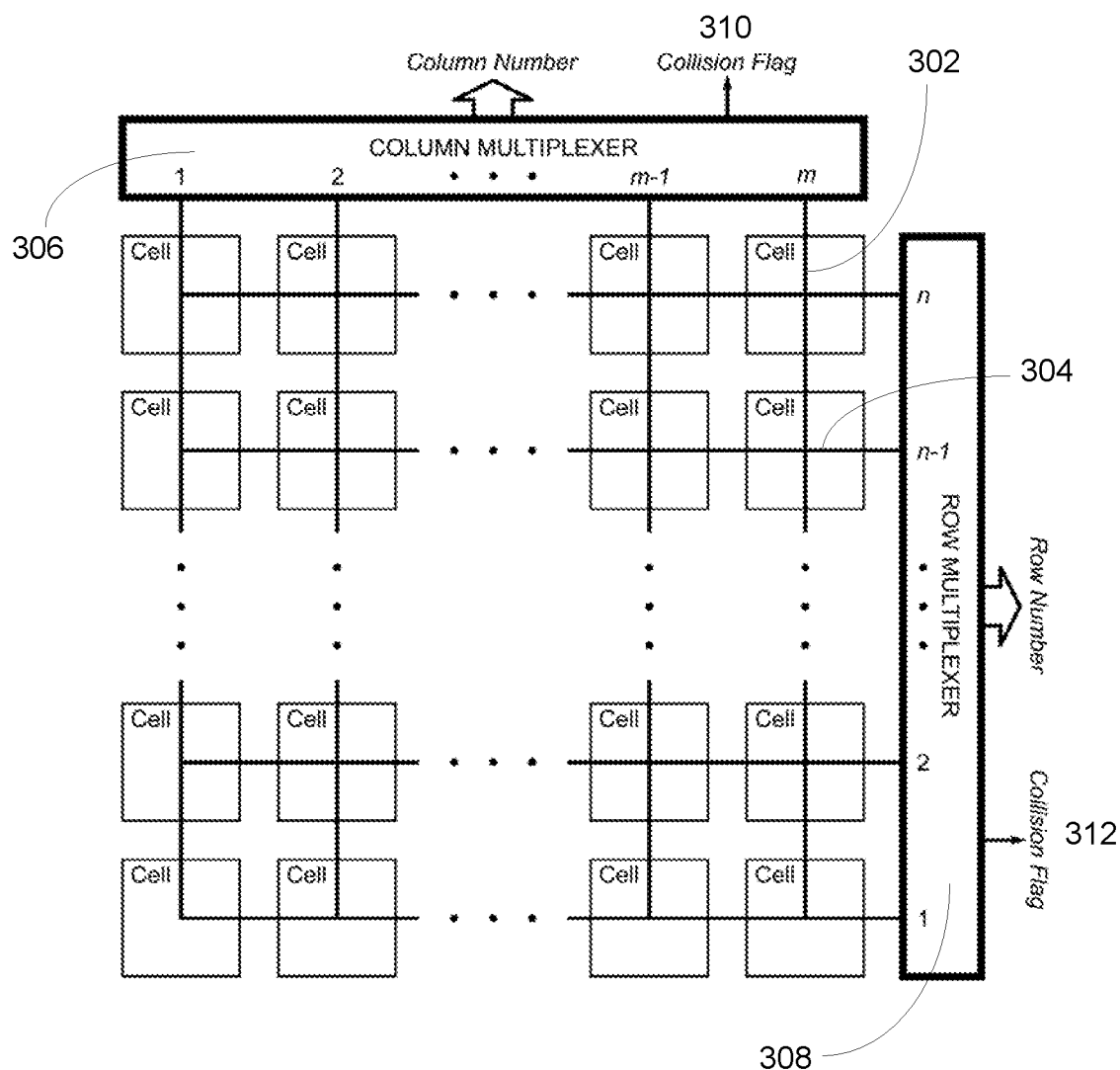
FIG. 6 is a block diagram illustrating an embodiment of a cell array in a biochip.

FIG. 6 is a block diagram illustrating an embodiment of a cell array in a biochip. Each of the cells may contain a sensor circuit 100 for measuring a physical property within the cell as described above. As shown in FIG. 6, the cell array has m columns by n rows of single cells. All the cells in a given column share the same column line 302, and all the cells in a given row share the same row line 304. When trip flag 116 for a particular cell is asserted, the cell asserts its particular column line 302 and row line 304. In order to reduce the pin count of the biochip, a column multiplexer 306 may be used to output a column number ($0$-$2^m$-$1$) to indicate which column line 302 has been asserted. Similarly, a row multiplexer 308 may be used to output a row number ($0$-$2^n$-$1$) to indicate which row line 304 has been asserted. For example, if trip flag 116 of the cell in the second column and the second row is asserted, the output column and row number is (1, 1). As long as only one cell asserts its trip flag 116 at a time, the reported column and row numbers are sufficient to uniquely identify which particular cell is asserted at a particular time.

The above techniques have a number of advantages over other approaches. The integrating amplifier requires minimal die area and allows for each array site to have its own dedicated measurement circuit. This feature removes the necessity of routing sensitive analog signals to the array periphery and avoids the need for multiplexing, thereby reducing noise. The integrating amplifier requires no pre-amplifier, sample and hold, or anti-aliasing filter, further reducing die area and potential error sources. Since only a single flag is required to denote the completion of a measurement, the integrating approach is an efficient way to communicate data from each array site. Measurements are being made continuously (other than the brief time required to reset the integration capacitor) so data is being gathered almost 100% of the time. Furthermore, each cell and its associated measurement circuit operate autonomously, allowing each cell to track the state of the molecule being measured. As described above, the integrating approach also has inherent signal averaging and noise advantages.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for detecting electrical properties of a nanopore sensor, comprising:
    an electrode electrically coupled to a nanopore sensor, the electrode configured to output an electrical signal affected by an electrical property of the nanopore sensor; and
    an integrating amplifier circuit configured to:
        receive the electrical signal from the electrode;
        integrate at least a portion of the electrical signal for a period of time until a threshold is reached; and
        output time information related to the period of time, wherein the time information is associated with an initiation flag and a trip flag, the initiation flag indicating a start to the integration of the electrical signal and the trip flag indicating an end to the integration of the electrical signal.

2. The system of claim 1, further comprising a processor programmed to determine a mean value of the electrical signal based on the threshold and the time information.

3. The system of claim 2, wherein the processor is further programmed to determine an average mean value of the electrical signal based on a plurality of determined mean values.

4. The system of claim 1, the electrical signal is not sampled during the period of time that the electrical signal is integrated.

5. The system of claim 1, wherein the threshold is predetermined.

6. The system of claim 1, wherein the threshold is adjustable.

7. The system of claim 1, wherein the electrical property is selected from the group consisting of a current, a voltage, a charge, and a capacitance.

8. The system of claim 1, wherein the integrating amplifier circuit is configured to preferentially amplify portions of the electrical signal within a set bandwidth.

9. The system of claim 8, wherein the set bandwidth is adjustable by varying the threshold.

10. The system of claim 8, wherein the set bandwidth is adjustable by varying a capacitance associated with the integrating amplifier circuit.

11. The system of claim 8, wherein the effect of the electrical property of the nanopore sensor on the electrical signal is characterized by an expected bandwidth, and wherein the set bandwidth is based at least in part on the expected bandwidth.

\* \* \* \* \*